United States Patent [19]
Wlodarczyk et al.

[11] Patent Number: 5,438,873
[45] Date of Patent: Aug. 8, 1995

[54] FIBEROPTIC SENSOR USING TAPERED AND BUNDLED FIBERS

[75] Inventors: Marek T. Wlodarczyk, Bloomfield Hills; Gang He, Ann Arbor, both of Mich.

[73] Assignee: Fiberoptic Sensor Technologies, Inc., Ann Arbor, Mich.

[21] Appl. No.: 255,411

[22] Filed: Jun. 8, 1994

Related U.S. Application Data

[63] Continuation-in-part of Ser. No. 87,631, Jul. 1, 1993, and a continuation-in-part of Ser. No. 86,245, Jul. 1, 1993.

[51] Int. Cl.⁶ .............................................. G01L 9/00
[52] U.S. Cl. .............................................. 73/705
[58] Field of Search ............... 73/705, 800, 862.624; 250/231.19, 227.14; 356/32; 385/43, 27

[56] References Cited

U.S. PATENT DOCUMENTS

| | | | |
|---|---|---|---|
| 4,142,774 | 3/1979 | Wright | 350/96.12 |
| 4,786,130 | 11/1988 | Georgiou et al. | 350/96.15 |
| 5,301,001 | 4/1994 | Murphy et al. | 356/345 |
| 5,315,364 | 5/1994 | Arion et al. | 356/32 |

OTHER PUBLICATIONS

"Tapered Fiber–Based Diaphragm–Type Pressure Sensor", Gange He, Marek T. Wlodarczyk, and Emery L. Moore, presented at SPIE '93, Boston, Mass., Sep. 1993, and to be published in Proc. SPIE.

"Dual-Wavelength Fiber Optic Temperature Sensor", Gange He and Marek T. Wlodarczyk, presented at SPIE'93, Boston, Sep. 1993 and to be published in Proc. SPIE.

Primary Examiner—Robert Raevis
Attorney, Agent, or Firm—Harness, Dickey & Pierce

[57] ABSTRACT

An improved fiberoptic pressure sensing system is disclosed by tapering the tip end of an optical fiber, or alternatively, by tapering or bundling a fiber or group of fibers within a connector. By selectively joining together fibers with a taper while tailoring numerical apertures of the connected fibers, a fiberoptic pressure sensing system is provided with an enhanced ability to increase sensitivity and signal-to-noise performance.

23 Claims, 2 Drawing Sheets

FIBEROPTIC SENSOR USING TAPERED AND BUNDLED FIBERS

This is a continuation-in-part of co-pending U.S. patent application Ser. Nos: 08/087,631, and 08/086,245, both filed on Jul. 1, 1993.

FIELD OF THE INVENTION

This invention relates to improvements in fiberoptic sensor systems, and in particular, to techniques for tapering optical fibers in fiber ends and fiber connectors to enhance optical detection sensitivity when measuring small mechanical deflections in diaphragm-type fiberoptic pressure sensors. Fiber tapering allows use of small sized fibers with high numerical apertures, and for bundling or joining multiple fibers when implementing signal multiplexing.

BACKGROUND OF THE PRESENT INVENTION

Miniature optical fiber pressure sensing systems have been used for a variety of applications. For example, the measurement of intravascular blood pressure of human patients has been accomplished using equipment manufactured by the present Assignee, FiberOptic Sensor Technologies, Inc. (FST), in which a diaphragm at the fiber sensing tip deforms in response to a pressure differential, thus modulating through reflection the light signal sent through the fiber. Changes in the distance between the deformed diaphragm and the optical fiber end, as well as the diaphragm shape, modulate the amplitude of light that is reflected back into the optical fiber. Accordingly, the intensity of the returned light signal is related to the pressure acting on the sensing tip.

Applicant has made numerous advancements in the technology of fiberoptic sensing systems which are principally oriented toward pressure measurement. The present Assignee, FST, also owns U.S. Pat. Nos. 4,701,246; 4,787,396; 4,856,317; 4,924,870; 5,247,171; 5,275,053; and 5,280,786, and co-pending U.S. applications with Ser. Nos. 08/132,718, filed on Oct. 6, 1993; 08/121,182, filed on Sep. 14, 1993; 08/128,849, filed on Sep. 29, 1993; and 08/109,361, filed on Aug. 19, 1993 which are related to various improvements in fiberoptic sensors and which are hereby incorporated by reference.

Furthermore, Applicant has made additional advancements in the technology of fiberoptic sensors for internal engine combustion chamber pressure measurement. These advancements are encompassed by Applicant's co-pending U.S. applications Ser. No. 08/087,631, and 08/086,245.

Particularly in health care applications, small size in-vivo pressure sensing catheters provide an accurate diagnostic tool when used in cardiology, urology, and trauma care, especially where invasive measurements and electrical bio-potential safety concerns necessitate use of small sensors and require electrical passiveness. Presently, use of the aforementioned intensity-based sensors utilize an optical fiber in front of a pressure sensing diaphragm which measures optical reflection to determine diaphragm displacement. These devices have proven to be practical, stable, small in size, and low in cost. However, one major limitation with use of these small-size diaphragm-type sensors is caused by their reduced sensitivity, i.e., a small diaphragm produces small deflections such that differential deflection must be more accurately quantified in order to obtain accuracy equivalent to that from a larger diaphragm sensor. Further design constraints increase the difficulty of providing such sensors having a desired frequency response range, long-term fatigue life, over-pressure protection, mechanical and optical stability and providing a structurally stable diaphragm when operating under a wide range of environmental conditions, including humidity and corrosion exposure. These requirements also restrict selection of a diaphragm's material, size, thickness, and strength parameters which reduce the ability to obtain an appropriate deflection range and sensitivity. In order to obtain improved sensor performance under the aforementioned mechanical constraints, techniques are needed to increase optical measurement sensitivity while still utilizing a small diaphragm sensor which compensates for the low mechanical responses of the diaphragm and improves overall performance over a broad range of applications.

SUMMARY OF THE INVENTION

In accordance with a principal feature of the present invention, a fiberoptic sensing system is provided with a tapered optical fiber section provided between a small sized fiber on a sensor system and a large fiber which provides for a gradual transition section from the small to large fibers and which increases displacement detection sensitivity, which provides for better signal-to-noise performance. Furthermore, a taper is provided in a connector design which provides an alignment and focusing mechanism at the optical interconnection. Additionally, the tapered section is provided with a high-reflectivity metal-coating for cases where light launched into the fiber has a high divergence angle which focuses the light to obtain reduced transmission losses and to increase sensitivity such that higher numerical aperture values are obtained. Alternatively, by carefully controlling the taper fabrication process, higher numerical aperture values can be obtained for a fiber which reduce transmission loses and increase sensitivity, for example by controlling the rate of taper, or by controlling the light launched into the connecting fiber such that it has low divergence angles.

In another important embodiment of the present invention, a tapered tip is provided on the end of a transmitting fiber which decreases the diameter of the fiber at the sensor's tip relative to the connecting optical fiber's diameter. Such a configuration provides improved sensitivity such that a small diaphragm producing small deflections can be used with a relatively large size optical fiber. Additionally, the tapered tip can be coated on its conical surface with a high-reflectivity metal-coating. The tapered sensor tip end enhances the overall system's signal-to-noise ratio which is preferably formed from a single fiber, or alternatively, is formed from a bundle of optical fibers which is fused and drawn together to form a decreasing bundle tip end which forms a sensor tip.

Another important embodiment of the present invention for enhancing signal to noise ratios in a diaphragm-type pressure sensor system employs a tapered sensor tip end which is formed from a single optical fiber, or alternatively, is formed by fusing and drawing an optical fiber bundle which decreases the bundle tip end diameter.

A further important embodiment of the present invention enhances fiberoptic sensor performance by providing a tapered fiber-optic bundle coupler for interconnecting a plurality of transmitting optical fibers to at least one sensor optical fiber by bundling the transmitting fibers, and preferably by providing a connector which couples the plurality of fibers forming a bundle into a common sensor output fiber.

Additional benefits and advantages of the present invention will become apparent to those skilled in the art to which this invention relates from the subsequent description of the preferred embodiments and the appended claims taken in conjunction with the accompanying drawings.

DETAILED DESCRIPTION OF THE PREFERRED EMBODIMENT

Pursuant to this invention, various improvements are disclosed for fiberoptic sensing systems which comprise tapering an optic fiber or bundle of optical fibers which facilitates joining a larger diameter fiber to a smaller diameter fiber in order to obtain a sensing system with a small fiber size and a high numerical aperture which increases optical detection sensitivity and signal modulation. By joining a small diameter sensor fiber to a larger diameter transmitting fiber through a tapered section, a sensing system having a desirable small fiber size at the sensor tip with a high numerical aperture can be obtained which obviates problems inherent in connecting such small-size fibers to optical modules due to critical alignment problems and low optical powering carrying capabilities associated generally with small-sized multi-mode optical fibers. By tapering an optical fiber, the signal modulation levels are significantly increased on the order up to 8 fold, which enhances performance of small-size diaphragm-type sensors as applied in a broad range of applications. Furthermore, implementation of a metalized taper layer on the conical surface of a taper in conjunction with optimization of the taper fabrication process produces a fiber taper sensor system that achieves a consistent and sensitive optical fiber taper-based sensor. Such a system can significantly increase the signal-to-noise ratio for a specific fiber optic system design.

Figure 1:
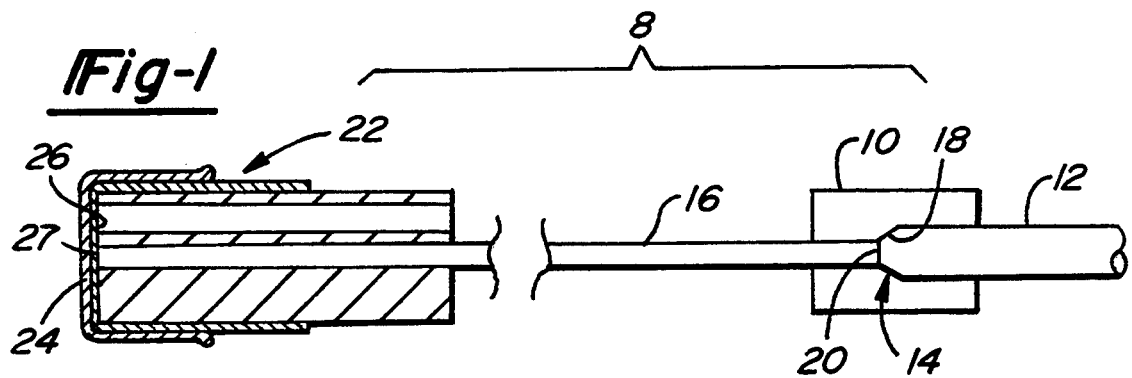
FIG. 1 is a somewhat diagrammatic cross-sectional view of a tapered fiberoptic sensor connector coupled to a single-fiber diaphragm-type sensor head of this invention.

Referring in more detail to the drawings, FIG. 1 illustrates a miniature intravascular blood pressure transducer 8 with a tapered optical connector 10 of this invention having a relatively large diameter optical transmitting fiber 12 with a tapered fiber end 14 which is received in the connector where it is mated and joined to a smaller diameter sensing optical fiber 16. Preferably, the optical transmitting fiber receives a reflective, or metal, layer 18 on the tapered fiber end where it forms a conical surface. A flat tip end 20 formed by the tapered end 14 of transmitting fiber 12 passes light from the transmitting fiber as well as light which is reflected and funneled in through reflective layer 18 into transmitting fiber 16 where it is carried to an optical sensing tip 22, such as a pressure sensing diaphragm optical fiber sensor. The optical connector 10 joins the transmitting and sensing fibers by optically aligning them so they emit and receive light therebetween. Preferably, a quick disconnect feature is provided whereby sensing fiber 16 can be removed and decoupled from connector 10, or alternatively, transmitting fiber 12 can be decoupled and removed from the connector 10, in order to removably connect a sensor in alignment with and to a transmitting fiber.

Preferably, the reflective layer 18 is provided on the tapered fiber end 14, exclusive of tip end 20, such that the tapered portion is covered or coated with a high-reflectivity metal-coating which reduces transmission losses and increases sensitivity of the sensor. Alternatively, the taper can be fabricated in a manner which controls the fiber's taper in order to obtain a high numerical aperture in the fiber at the region of the taper which reduces transmission losses and increases sensitivity. By limiting the taper ratio, significant taper transmission losses which are produced by higher order modes escaping the fiber can be avoided. With higher numerical apertures, there are less high-order mode losses which leads to increased optical power throughput which results in better signal-to-noise performance in the fiber.

In cases where the taper 14 is formed by a heat process, high-temperature-induced dopant redistribution and geometrical deformation modifies the fiber's cladding layer in the region of the taper such that the region acts as a modified wave guide which primarily depends on the fiber-to-air interface to confine propagating optical modes. As a result, large refractive index differences between the taper section and the air provide increased effective numerical apertures in the region of the taper. Alternatively, a heat tapered tip can be recoated after tapering to maintain the same effective numerical aperture, or further alternatively, that the effective cladding layer is retained during a controlled process. In this case, the effective numerical aperture of the input fiber is smaller and significant taper transmission losses will result from higher order modes escaping the tapered section, and losses can only be avoided by launching light into the fiber which has a low-divergence angle. For uses where low-divergence light is transmitted through the optical fiber, this is not a problem. However, when used with a LED source in intensity-based sensor systems, wide-angle radiation patterns are present and a controlled taper fabrication process must be utilized, or the reflective layer or coating 18 must be provided about the taper.

The preceding arrangement provides a transmitting fiber 12 having a larger diameter than the sensing fiber 16 which provides certain advantages in constructing a sensor system that increases the signal to noise ratio without significantly increasing the sensor cost. For example, one property of a diaphragm sensor is a direct relationship which exists between pressure increase and diaphragm deflection toward the optical sensing tip 22. The quantity of light collected by a sensing fiber end 24 which is reflected by a respectively coated sensor diaphragm 26 increases monotonically with pressure. By carefully selecting sensing and transmitting fiber core diameters and numerical apertures, optical modulation depth can be increased for a given sensor size and diaphragm stiffness. The sensor's modulation is inversely related in a nearly linear manner to the sensor fiber size, and approximately linear with numerical aperture. Therefore, fibers with small diameters and large numerical apertures should be used to obtain maximum modulation. Likewise, a high numerical aperture also favors optical power carrying capability for a specific fiber. The power carrying capability is a function of a squared value for the numerical aperture. However, it is undesirable to reduce fiber diameter because the power level also generally decreases by a squared function of the diameter. By optically coupling a large diameter transmitting fiber to a smaller diameter sensing fiber via a taper, both the benefit of maximum modulation obtained with a small diameter fiber can be obtained while minimizing the reduced power level due to decreased diameter.

Although the modulation depth is significantly increased by using a decreased diameter optical sensing fiber 16 in sensing tip 22, transmission losses are increased due to leakage of high-order guided modes in the tapered fiber end 14 of connector 10. Reflective layer 18 is therefore provided to reduce these transmission losses as was described infra.

Figure 2:
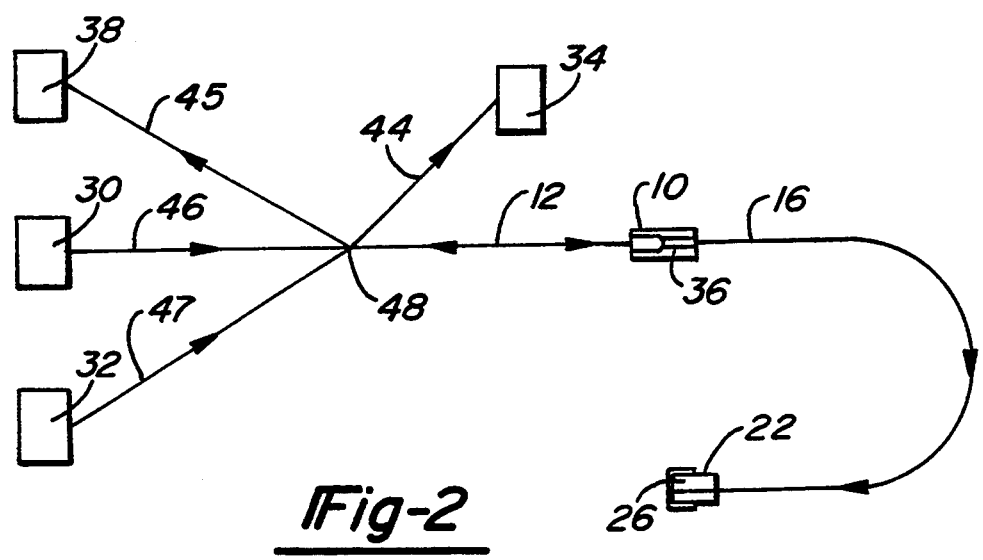
FIG. 2 is a schematic diagram of a first embodiment fiberoptic sensor system utilizing the connector of FIG. 1 to perform time division multiplexing.

FIG. 2 illustrates an alternative arrangement for delivering and collecting optical signals for the transducer 8 as depicted in FIG. 1. In FIG. 2, a pair of light sources, or light emitting diodes 30 and 32 supply light signals having two distinctly different wavelengths to the transmitting fiber 12. Fiberoptic branches 44-47 are joined together to form tapered and fused bundle 48 which is finally fused into a single optical transmitting fiber 12 for connection with the tapered optical connector 10 of this invention to the reduced diameter optical sensing fiber 16. Preferably, the tapered and fused bundle 48 is formed by tapering and fusing the respective branches together which provides an enlarged diameter which is tapered within an optical connector 10 of this invention and joined to the reduced diameter optical sensing fiber 16. A reference light detector 34 is provided for monitoring the light intensity of each diode through suitable circuitry which maintains light output from each diode substantially constant. In this embodiment, a single measuring detector 38 is utilized to alternatively monitor the light intensity of each diode 30 and 32.

Preferably, a transmissive and reflective coating 36 is provided in the connector 10 on the sensor fiber side 16 which forms a film or coating that abuts with flat lip end 20 and which acts to filter one of the wavelength signals from one of the diodes 30 or 32. Coating 36 permits passage of one signal from one of the diodes while reflecting the other signal from the other diode which has a differing wavelength and which acts as a reference signal. The reference signal has a wavelength denoted $W_c$ which is reflected by coating 36, and the passed signal has wavelength $W_s$. Alternatively, as shown in FIG. 1, an identical transmissive and reflective coating 27 can be deposited on the sensor tip end 16 in the sensor tip 22. Wavelength $W_s$ is therefore used to measure diaphragm deflection.

Figure 3:
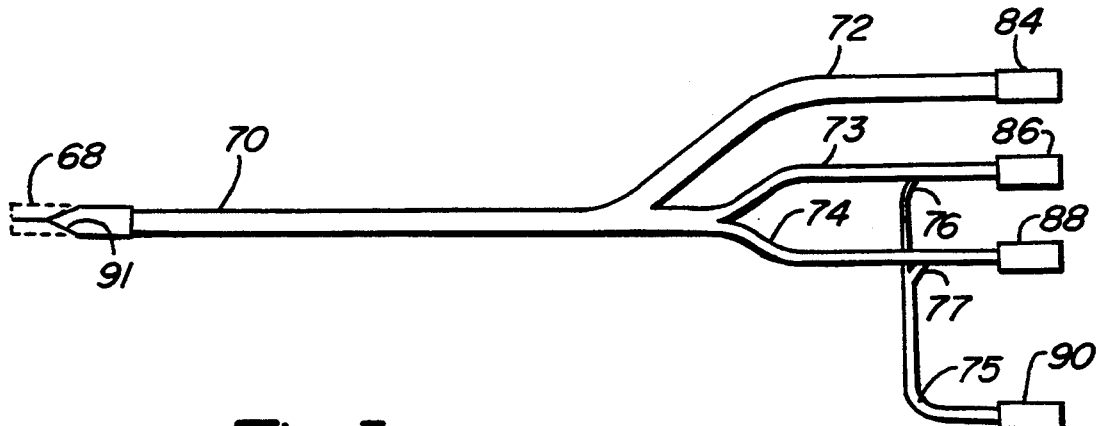
FIG. 3 is a schematic diagram of a third embodiment fiberoptic sensor system showing a fiberoptic bundle of transmitting fibers which are joined and fused together where they enter the connector of FIG. 1 which allows for connection to a smaller diameter sensing fiber.

FIG. 3 illustrates an alternative embodiment for the optical connector 10 of transducer 8 in FIG. 1 which is labelled as reference numeral 68. A fiber bundle 70 is formed from groups of transmitting fibers 72 through 74 which are joined at a fused and tapered end 91 formed in the optical connector 68. The connector is analogous to connector 10 of FIG. 1 which connects to a sensing fiber 16 (not shown). The fiber bundle 70 extends from the connector where it diverges into fiber subgroups for dedication to various optical-electronic elements. For example, transmitting fiber subgroup 72 is composed of an array of 16 fibers which connect to a reference light detector, preferably a photo diode, in a measurement detector 84. Fiber subgroup 73 interconnects through 8 fibers with a first light emitting diode (LED) 86. Likewise, fiber subgroup 74 connects with a second LED 88 through an array of 8 fibers. Furthermore, a reference detector 90 is interconnected to each LED 86 and 88 through fiber sub-bundles 76 and 77 which join to form bundle 75. With the preceding arrangement, light from the pair of LED's is efficiently coupled by fiber bundling to form an effective transmitting fiber 70 which is joined through the connector 68 by a taper to the sensing fiber (not shown).

For example, a group of 50 micron borosilicate fibers which are extensively used in fiber imaging scopes may be utilized to form the aforementioned fiber bundle 70. Up to 100 fibers can be utilized to form a transmitting fiber bundle, depending on selection of LED's and sensing fiber diameters. Alternatively, fibers with larger diameters can be used in bundles with fewer fibers. Irrespective of the number of fibers used, the fibers in a fiber bundle transmit light from the LED's as well as return light to the measurement detector such that they are fused and tapered at the connector end to a final diameter which is suitably matched with a sensing fiber. The resulting taper, which may be fabricated in a straight forward way through thermal fusing of borosilicate fibers such that they are pulled during fusing, produces an important efficient transition from a relatively large bundle size, perhaps 500 microns in diameter, to a sensing fiber size of typically 100 to 200 microns in diameter. But for the taper, a size mismatch loss might reduce the returning optical signal to unacceptable levels. As a result, low cost LEDs with divergent and large light beams can efficiently couple power into the fiber, which otherwise can not be effectively used with a small-size fiber. The bundle of fibers collects the light from the LED's such that with borosilicate fibers having typically high numerical apertures of 0.5 to 0.6, the fiber bundles collection efficiency is increased. Furthermore, at the tapered end of a fiber bundle, taper loss is reduced through use of a metal coating 91 over the taper which is formed inside the connector 68.

Figure 4:
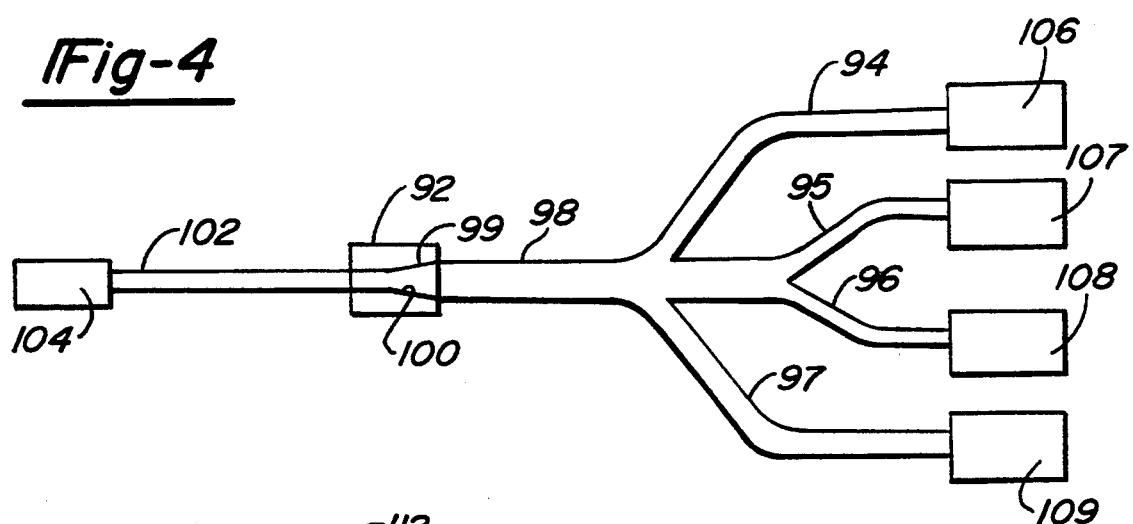
FIG. 4 is a schematic diagram of a fourth embodiment fiberoptic sensor system utilizing the connector of FIG. 1 arranged in a reverse direction for connecting a plurality of sensing fibers which are fused and joined together to a common transmitting fiber.

FIG. 4 illustrates a further alternative embodiment for the optical connector 10 and the transducer 8 of FIG. 1. An optical connector 92 similar to connector 10 is arranged in a reverse direction with respect to a group of sensor fibers 94-97 which are joined together to form a bundle 98 having a fused and tapered tip 99 which has a reflective layer 100 on the taper. Preferably, the connector aligns and retains the fused and tapered tip with the end of a transmitting fiber 102 which is connected to a transducer 104. By using connector 92, a group of sensors 106–109 can be joined together with a common connector in order to utilize a single transmitting fiber and a single optics module to monitor optical measurements made from a plurality of sensors. For example, multiple sensors on an engine can be monitored with a single optics module.

Figure 5:
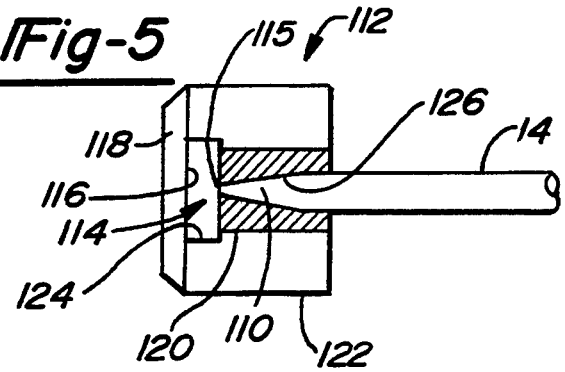
FIG. 5 is a somewhat diagrammatic cross-sectional view of a diaphragm-type fiberoptic sensor with a tapered fiberoptic tip of this invention.

FIG. 5 illustrates a modified version of the optical sensing tip 22 of FIG. 1 which utilizes a tapered tip end 110 on a sensing fiber 16 to provide a tapered fiber tip sensor 112. Preferably, the optical sensing fiber 16 terminates into the tapered tip end 54 such that an air gap, or cavity, 114 is provided between the end of the tip 115 and a reflective back face 116 on a sensor diaphragm 118. Preferably, the tapered tip end is received in a conical ferrule 120 carried in a sensor body 122. Furthermore, a small cylindrical cavity 124 is provided adjacent the diaphragm. Pressure imparted by the external environment on the membrane 118 displaces the membrane toward the tip end 115 which decreases the air gap 114 formed between the tip and membrane. As a result, light reflected back from the membrane is modulated. As discussed supra, the conical taper 110 on tip 115 increases modulation depth significantly, but transmission losses are also increased. To reduce these losses, a thin metallic reflective layer 126, similar to layer 18 in FIG. 1, is provided on the taper surface 110 of the tip. The transmission losses are significantly reduced as a result, and furthermore through suitable selection of metals, such as gold, a metal layer is provided for interface bonding material when brazing the conical ferrule to an optical sensing fiber 14.

Figure 6:
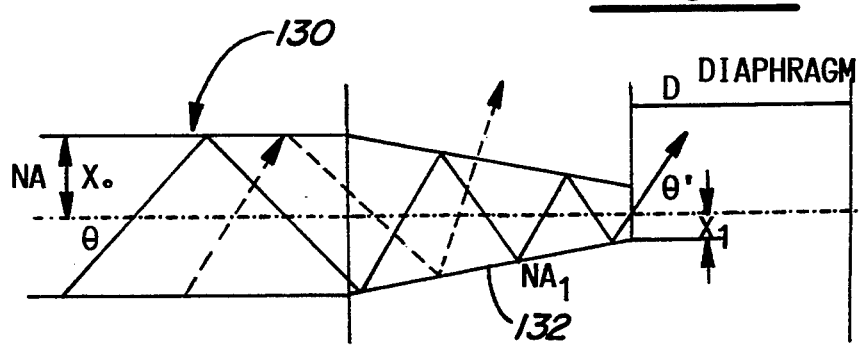
FIG. 6 is a somewhat diagrammatic cross-sectional view of a tapered optical fiber.

FIG. 6 shows a light ray propagating in a tapered optical fiber 130 which travels and propagates at an angle $\Theta$ and which shows the propagation angle increments inside the tapered section 132 as it is reflected. If an appropriate numerical aperture is provided in the tapered region, the ray of light transmitting through the fiber will satisfy the total-internal-reflection condition within the tapered region such that it will emerge from the end of the tapered portion of the fiber with a higher angle $\Theta'$. For the case where higher order modes travel through the fiber with propagating angles which exceed the limiting angle determined by the fiber's numerical aperture in the tapered region, designated by $NA_t$, the higher order modes will escape through the side of the taper, and contribute to optical power losses. Obviously, these higher numerical apertures in the tapered tip $NA_t$ will result in less high-order mode losses, which will allow an increased optical power through-put which provides better signal-to-noise performance. Where an effective cladding layer has been retained when constructing the tapered tip, or the tapered tip has been recoated after it has been tapered, the effective tapered numerical aperture will be identical to the original fiber's numerical aperture, (NA) in the adiabatic or gradually tapered fibers. For these cases, in order to avoid significant taper transmission losses resulting from higher order modes escaping the tapered sections as shown in FIG. 6, light launched into the fiber must have low divergence angles. This effectively reduces the input fiber's numerical aperture to $NA'$ by a relation $NA' = NA/t'$ where $t = X_o/X_t$ is the taper ratio, such that only beams with propagating angles less than $\sin^{-1}(NA')$ can satisfy the total-internal-reflection condition upon multi-reflections in the tapered region, and emerge from the tapered section 132. Construction of optical fiber tapers with these criterion have been used to deliver low-divergence, large-spot-sized laser beams to small areas or into small-sized optical fibers. However, as mentioned supra, use of LED sources in intensity-based sensor systems exhibits wide-angle radiation patterns, and generally will not satisfy the criterion of the aforementioned equation. Therefore, the controlled taper fabrication process must be implemented in order to achieve higher numerical apertures in the taper in order to obtain reduced transmission losses and to increase sensitivity. Alternatively, utilization of high-reflectivity metal-coatings in the tapered section as provided in the previous embodiments reduces the taper transmission losses to an acceptable level in order to alleviate these problems.

In constructing such a tapered tip, typically a fused-silica optical fiber is locally softened with a propane torch, and it is simultaneously pulled apart on a mechanical device. Likewise, the taper 18 of transmission fiber 12 in FIG. 1 can be formed in a similar manner. This process will produce a tapered section of several millimeters in length. Preferably, the tapered section geometry and surface quality are consistently controlled when tapering the fiber in order to obtain predictable and consistent numerical aperture increases. Furthermore, metal-coated tapers are utilized to obtain a higher taper ratio which does not provide the aforementioned losses and disadvantages. As a result, the optical fiber taper-based sensor designs mentioned previously provide a practical and reliable opto-electronic system configuration, and offer significantly improved optical detection sensitivity. Furthermore, the design can be readily adapted to various applications which require sensitive optical measurement of inherently small mechanical diaphragm deflections.

Figure 7:
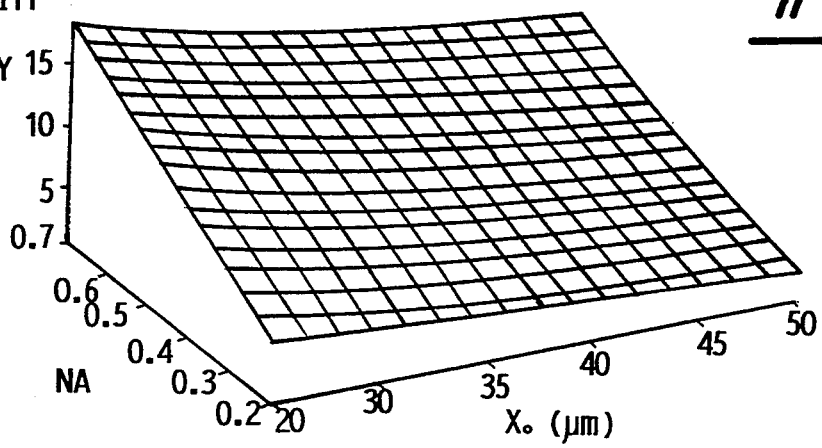
FIG. 7 is a three dimensional plot of optical detection sensitivity for a range of fiber core radius and numerical aperture.

FIG. 7 is a three dimensional plot summarizing detection sensitivity values, m, over a range of fiber core radius, $X_0$, and a range of numerical aperture, NA. As shown in FIG. 7, m values are sensitivity with arbitrary unit and are given for 25 $\mu m \leq X_0 \leq 50$ $\mu m$ and $0.2 \leq NA 0.7$. Coupled with increased m values, if a suitable optical power output level is maintained via proper system design, a significantly improved pressure measurement performance and system stability is realized. This is attributed to the following factors: (1) System signal-to-noise performance will be significantly improved, since SNR for shot noise-limited systems is proportional to m and to the square root of optical power output. In case that electrical thermal noise and circuit interference are the dominant noise sources, SNR will be proportional both to m and to optical power output. (2) Measurement errors induced by factors such as fiber bending, temperature-related signal drift, and optical interconnection throughput variations are proportionally reduced by m increments, since the error signals are only proportional to disturbance levels and system optical power output.

It is to be understood that the invention is not limited to the exact construction illustrated and described above, but that various changes and modifications may be made without departing from the spirit and scope of the invention as defined in the following claims.

We claim:

1. In a fiberoptic pressure sensing system having an optical fiber with a sensing tip at a first end with a pressure sensitive element, the pressure sensitive element modulating a pressure sensing light signal injected into an opposite second end of the optical fiber, the improvement comprising:

a first optical fiber portion formed by the optical fiber with a distal end forming the sensing tip;

a second optical fiber portion adjoining said first portion at a proximal end; and a tapered fiber segment formed by the optical fiber at an intermediate location so as to light couple said first and second portions together.

2. The fiberoptic pressure sensing system of claim 1 wherein said first optical fiber portion has a low numerical aperture relative to said second optical fiber portion at the region of connection therebetween.

3. The fiberoptic pressure sensing system of claim 1 wherein said first and second portions are substantially the same numerical aperture.

4. The fiberoptic pressure sensing system of claim 1 further comprising connection means formed between said first and second optical fiber portions.

5. The fiberoptic pressure sensing system of claim 4 further comprising a partially reflective optical filter provided between said first optical fiber portion and said second optical fiber portion.

6. The fiberoptic pressure sensing system of claim 1 wherein said second optical fiber portion comprises a fiber bundle, said bundle being divided into a plurality of subgroups of fibers at a distal end of said bundle remote from said first optical fiber portion.

7. The fiberoptic pressure sensing system of claim 6 wherein said subgroups are individually coupled to opto-electronic devices.

8. The fiberoptic pressure sensing system of claim 6 further comprising connection means formed between said first and second optical fiber portions.

9. The fiberoptic pressure sensing system of claim 8 wherein said bundle is tapered in said connection means.

10. The fiberoptic pressure sensing system of claim 8 wherein said second optical fiber portion comprises a fiber bundle, said bundle being tapered in said connection means and being metal coated over said taper.

11. The fiberoptic pressure sensing system of claim 1 wherein said first optical fiber portion comprises a fiber bundle, said bundle being divided into a plurality of subgroups of fibers at a distal end of said bundle remote from said second optical fiber portion, said fiber bundle providing said tapered fiber segment at a proximal end of said bundle adjoining said second optical fiber portion.

12. A fiberoptic pressure sensing system having an optical fiber with a sensing tip at a first end with a pressure sensitive element, the pressure sensitive element modulating a pressure sensing light signal injected into an opposite second end of the optical fiber and returning the light signal into the fiber, the improvement comprising:

a tip end provided on the optical fiber; and a taper formed adjacent said tip end which decreases the fiber diameter at said tip end.

13. The fiberoptic pressure sensing system of claim 12 wherein said taper has a decreasing diameter formed by fusing and drawing said tip end to form a reduced diameter, for example 75%.

14. The fiberoptic pressure sensing system of claim 13 wherein the decrease in said tip end diameter being fused and drawn forms said taper, said taper further receiving a coated layer of reflective metal.

15. The fiberoptic pressure sensing system of claim 13 further comprising a partially reflective optical filter provided on said tip end.

16. The fiberoptic pressure sensing system of claim 15 wherein the decreased diameter fused and drawn fiber bundle tip end forms said tapered tip end, said tapered tip end being coated with a layer of reflective metal.

17. The fiberoptic pressure sensing system of claim 12 wherein the optical fiber comprises a fiber bundle adjoining said tip end, said bundle further having a fused and drawn portion which decreases the bundle diameter proximate said tip end.

18. The fiberoptic pressure sensing system of claim 17 wherein said fiber bundle extends to at least one source of light and at least one detector, said bundle fibers being divided into a plurality of subgroups of fibers at the detector and light source end, one subgroup of fibers being connected to the detector and another subgroup being connected to the light source.

19. The fiberoptic pressure sensing system of claim 18 further comprising a second detector and a corresponding second separate subgroup of fibers, said second separate subgroup of fibers connecting said second detector to said light sensor.

20. The fiberoptic pressure sensing system of claim 19 further comprising a second light source and a corresponding second subgroup of fibers connecting said second light source with said fiber bundle, said second light source being connected to said second detector by said second separate subgroup of fibers.

21. The fiberoptic pressure sensing system of claim 17 wherein said fiber bundle has a fused and drawn tip end with a decreased diameter.

22. A fiberoptic pressure sensing system having an optical fiber with a sensing tip at a first end with a pressure sensitive element, the pressure sensitive element modulating a pressure sensing light signal injected into the opposite second end of the optical fiber, the improvement comprising:

a first optical fiber portion providing one portion of the optical fiber with a distal end forming the sensing tip;

a second optical fiber portion adjoining said first portion at a proximal end; and a taper formed by said optical fiber interjacent said first and second portions.

23. The fiberoptic pressure sensing system of claim 22 further comprising a connector communicating with said first optical portion at the proximal end and said second optical fiber portion at a distal end; wherein said taper is provided by said second optical portion at a distal end which is received within said connector and optically mated with said first optical portion proximal end.

* * * * *